US012232860B2

(12) United States Patent
Cai et al.

(10) Patent No.: US 12,232,860 B2
(45) Date of Patent: Feb. 25, 2025

(54) METHOD AND SYSTEM FOR HIGH-RESOLUTION MULTI-PARAMETRIC QUANTITATIVE MAGNETIC RESONANCE IMAGING

(71) Applicant: Xiamen University, Fujian (CN)

(72) Inventors: Shuhui Cai, Fujian (CN); Wenhua Geng, Fujian (CN); Qizhi Yang, Fujian (CN); Congbo Cai, Fujian (CN); Zhong Chen, Fujian (CN)

(73) Assignee: Xiamen University, Fujian (CN)

( * ) Notice: Subject to any disclaimer, the term of this patent is extended or adjusted under 35 U.S.C. 154(b) by 71 days.

(21) Appl. No.: 18/203,712

(22) Filed: May 31, 2023

(65) Prior Publication Data

US 2024/0197196 A1 Jun. 20, 2024

(30) Foreign Application Priority Data

Dec. 15, 2022 (CN) .......................... 202211618584.X

(51) Int. Cl.
*A61B 5/055* (2006.01)
*G06T 5/10* (2006.01)
*G06T 7/00* (2017.01)
*G06V 10/82* (2022.01)

(52) U.S. Cl.
CPC .............. *A61B 5/055* (2013.01); *G06T 5/10* (2013.01); *G06T 7/0012* (2013.01); *G06V 10/82* (2022.01); *G06T 2207/10088* (2013.01)

(58) Field of Classification Search
CPC ............ G06T 5/10; G06T 7/0012; G06T 2207/10088; G01R 33/4835; G01R 33/54; G01R 33/5608; G01R 33/5611; G01R 33/5617; G01R 33/565; A61B 5/055; G06V 10/82
See application file for complete search history.

(56) References Cited

U.S. PATENT DOCUMENTS

2021/0134028 A1* 5/2021 Cai .................. G01R 33/50

* cited by examiner

*Primary Examiner* — Boniface N Nganga
(74) *Attorney, Agent, or Firm* — Cooper Legal Group, LLC

(57) ABSTRACT

A method for fast high-resolution multi-parametric quantitative magnetic resonance imaging comprises: designing a fast high-resolution multiple overlapping-echo imaging pulse sequence; determining sampling parameters of the pulse sequence; constructing a deep neural network for reconstructing high-resolution multi-parametric quantitative magnetic resonance images; generating training samples of the deep neural network; using the training samples to train the deep neural network to obtain trained deep neural networks; scanning a real imaging object using the pulse sequence under the sampling parameters to obtain k-space data of the real imaging object; pre-processing the k-space data of the real imaging object to obtain image domain data of the real imaging object; and inputting the image domain data of the real imaging object into the trained deep neural networks for the reconstructing to obtain the high-resolution multi-parametric quantitative magnetic resonance images of the real imaging object.

6 Claims, 5 Drawing Sheets

METHOD AND SYSTEM FOR HIGH-RESOLUTION MULTI-PARAMETRIC QUANTITATIVE MAGNETIC RESONANCE IMAGING

RELATED APPLICATIONS

This application claims priority to Chinese patent application 202211618584.X, filed on Dec. 15, 2022. Chinese patent application 202211618584.X is incorporated herein by reference.

FIELD OF THE DISCLOSURE

The present disclosure relates to the field of the magnetic resonance imaging, and specifically relates to a method and a system for fast high-resolution multi-parametric quantitative magnetic resonance imaging.

BACKGROUND OF THE DISCLOSURE

Magnetic resonance imaging can image biological tissues without invasion and injury. Quantitative magnetic resonance imaging has advantages of good repeatability, insensitive to instrument differences, and great clinical diagnostic value. Traditional quantitative magnetic resonance imaging needs to collect multiple images with different parameter-weighting for fitting, so its acquisition time is long. In addition, during the long acquisition period, motion of an imaging object will cause artifacts and other problems. In order to shorten an acquisition time, a series of methods for fast quantitative magnetic resonance imaging based on over-lapping-echo technology have been proposed, such as described in CN108663644B, CN108010100B, CN110807492A, etc. However, the aforementioned methods are based on planar echo imaging, so spatial resolution is limited, and the results are easily affected by inhomogeneous magnetic fields.

BRIEF SUMMARY OF THE DISCLOSURE

In order to solve the above problems, the present disclosure proposes a method and a system for fast high-resolution multi-parametric quantitative magnetic resonance imaging to fast achieve high-resolution multi-parametric quantitative magnetic resonance images and have an ability to resist image distortion caused by inhomogeneous magnetic fields to a certain extent.

The present disclosure discloses the following technique solutions.

A method for fast high-resolution multi-parametric quantitative magnetic resonance imaging comprises: designing a fast high-resolution multiple overlapping-echo imaging pulse sequence; determining sampling parameters of the fast high-resolution multiple overlapping-echo imaging pulse sequence; constructing a deep neural network for reconstructing high-resolution multi-parametric quantitative magnetic resonance images; generating training samples of the deep neural network; using the training samples to train the deep neural network to obtain trained deep neural networks; scanning a real imaging object using the fast high-resolution multiple overlapping-echo imaging pulse sequence under the sampling parameters to obtain first k-space data of the real imaging object; pre-processing the first k-space data of the real imaging object to obtain image domain data of the real imaging object; and inputting the image domain data of the real imaging object into the trained deep neural networks for the reconstructing to obtain the high-resolution multi-parametric quantitative magnetic resonance images of the real imaging object. The fast high-resolution multiple over-lapping-echo imaging pulse sequence comprises a signal excitation module and a data acquisition module, the signal excitation module comprises N radio frequency (RF) excitation pulses with time intervals $t_n$ and flip angles $\alpha_n$, slice selection gradients $G_{ss}$ corresponding to the N RF excitation pulses, and echo shift gradients $G_n$, and $n=1, 2, \ldots, N$, and $N \geq 2$. Each of the N RF excitation pulses is combined with a corresponding one of the slice selection gradients $G_{ss}$ in a slice selection dimension for slice selection. The echo shift gradients $G_n$ are applied after a corresponding RF excitation pulse of the N RF excitation pulses along a frequency encoding dimension and a phase encoding dimension. The data acquisition module comprises a pre-phase gradient $G_{pre}$, M refocusing pulses with time intervals ESP and flip angles $\beta_m$, crushing gradients $G_{cr}$, phase encoding gradients $G_{pe,i,m}$, frequency encoding gradients $G_{ro}$, and dephase encoding gradients $G_{pe,i,m}'$, i represents an ith scanning, and $m=1, 2, \ldots, M$, and $M \geq 2$. The pre-phase gradient $G_{pre}$ is applied along the frequency encoding dimension, and a size of the pre-phase gradient $G_{pre}$ is half of a corresponding one of the frequency encoding gradients $G_{ro}$. The crushing gradients $G_{cr}$ are applied before and after each refocusing pulse of the M refocusing pulses, sizes and directions of the crushing gradients $G_{cr}$ are the same along the frequency encoding dimension, the phase encoding dimension, and the slice selection dimension. The phase encoding gradients $G_{pe,i,m}$, the frequency encoding gradients $G_{ro}$, and the dephase encoding gradients $G_{pe,i,m}'$ are applied after each refocusing pulse of the M refocusing pulses, and the phase encoding gradients $G_{pe,i,m}$ and the dephase encoding gradients $G_{pe,i,m}'$ have same sizes but opposite directions.

In a preferred embodiment, the determining sampling parameters of the fast high-resolution multiple overlapping-echo imaging pulse sequence comprises: determining a number N of the N RF excitation pulses and a flip angle $\alpha_n$ of each RF excitation pulse of the N RF excitation pulses; determining a composition of echo signals to determine a time interval $t_n$ between two neighboring RF excitation pulses of the N RF excitation pulses; determining a position of each of the echo signals in a k-space so as to determine a proportion of the echo shift gradients $G_n$ after each RF excitation pulse of the N RF excitation pulses; determining a number M of the M refocusing pulses and a flip angle $\beta_m$ of each refocused pulse of the M refocusing pulses; determining a phase encoding manner to determine a direction and a proportion of each of the phase encoding gradients $G_{pe,i,m}$ and each of the dephase encoding gradients $G_{pe,i,m}'$; and determining a scanning number, an imaging field of view, an imaging matrix, a sampling frequency, a time interval ESP between two neighboring refocusing pulses of the M refocusing pulses, a sampling acceleration factor, and a repetition time TR of the fast high-resolution multiple overlapping-echo imaging pulse sequence so as to determine values of various gradients in the fast high-resolution multiple overlapping-echo imaging pulse sequence.

In a preferred embodiment, the constructing a deep neural network for reconstructing high-resolution multi-parametric quantitative magnetic resonance images comprises: constructing a network structure of the deep neural network; constructing a number of input channels of the deep neural network and a number of output channels of the deep neural network; and constructing a loss function of the deep neural network.

In a preferred embodiment, the generating training samples of the deep neural network comprises: preparing a simulated proton density image, a simulated $T_1$ quantitative image, a simulated $T_2$ quantitative image, and a simulated $T_2^*$ quantitative image according to characteristics of the real imaging object to form a virtual imaging object; establishing non-ideal factor models based on non-ideal factors existing in actual scanning; performing Bloch simulation on the virtual imaging object using the fast high-resolution multiple overlapping-echo imaging pulse sequence and the non-ideal factor models to obtain first k-space data of the virtual imaging object; separating odd and even rows of the first k-space data of the virtual imaging object to fill into two k-spaces to respectively obtain two second k-space data of the virtual imaging object, performing an inverse Fourier transform to obtain image domain data of the virtual imaging object to form a training sample of the training samples together with the virtual imaging object and the non-ideal factor models; and repeating the aforementioned steps to generate a set number of the training samples.

In a preferred embodiment, the pre-processing the first k-space data of the real imaging object to obtain the image domain data of the real imaging object comprises: separating collected odd and even rows of the first k-space data of the real imaging object to respectively fill into two k-spaces according to the phase encoding manner to obtain two second k-space data of the real imaging object; parallel reconstructing the two second k-space data of the real imaging object provided that a sampling acceleration factor is more than 1; and performing an inverse Fourier transform for the two second k-space data to obtain the image domain data of the real imaging object.

A system for fast high-resolution multi-parametric quantitative magnetic resonance imaging comprises a pulse sequence design module for designing a fast high-resolution multiple overlapping-echo imaging pulse sequence; a sampling parameter determination module for determining sampling parameters of the fast high-resolution multiple overlapping-echo imaging pulse sequence; a deep neural network construction module for constructing a deep neural network for reconstructing high-resolution multi-parametric quantitative magnetic resonance images; a training sample generation module for generating training samples of the deep neural network; a deep neural network training module for using the training samples to train the deep neural network to obtain trained deep neural networks; a k-space data acquisition module for scanning a real imaging object using the fast high-resolution multiple overlapping-echo imaging pulse sequence under the sampling parameters to obtain k-space data of the real imaging object; an image domain data acquisition module for pre-processing the k-space data of the real imaging object to obtain image domain data of the real imaging object; and a multi-parametric quantitative magnetic resonance image acquisition module for inputting the image domain data of the real imaging object into the trained deep neural networks for the reconstructing to obtain the high-resolution multi-parametric quantitative magnetic resonance images of the real imaging object. The fast high-resolution multiple overlapping-echo imaging pulse sequence comprises a signal excitation module and a data acquisition module, the signal excitation module comprises N radio frequency (RF) excitation pulses with time intervals $t_n$ and flip angles $\alpha_n$, slice selection gradients $G_{ss}$ corresponding to the N RF excitation pulses, and echo shift gradients $G_n$, and n=1, 2, ..., N, and N≥2. Each of the N RF excitation pulses is combined with a corresponding one of the slice selection gradients $G_{ss}$ in a slice selection dimension for slice selection. The echo shift gradients $G_n$ are applied after a corresponding RF excitation pulse of the N RF excitation pulses along a frequency encoding dimension and a phase encoding dimension. The data acquisition module comprises a pre-phase gradient $G_{pre}$, M refocusing pulses with time intervals ESP and flip angles $\beta_m$, crushing gradients $G_{cr}$, phase encoding gradients $G_{pe,i,m}$, frequency encoding gradients $G_{ro}$, and dephase encoding gradients $G_{pe,i,m}'$, i represents an ith scanning, and m=1, 2, ..., M, and M≥2. The pre-phase gradient $G_{pre}$ is applied along the frequency encoding dimension, and a size of the pre-phase gradient $G_{pre}$ is half of a corresponding one of the frequency encoding gradients $G_{ro}$. The crushing gradients $G_{cr}$ are applied before and after each refocusing pulse of the M refocusing pulses, and sizes and directions of the crushing gradients $G_{cr}$ are the same along the frequency encoding dimension, the phase encoding dimension, and the slice selection dimension. The phase encoding gradients $G_{pe,i,m}$, the frequency encoding gradients $G_{ro}$, and the dephase encoding gradients $G_{pe,i,m}'$ are applied after each refocusing pulse of the M refocusing pulses, and the phase encoding gradients $G_{pe,i,m}$ and the dephase encoding gradients $G_{pe,i,m}'$ have same sizes but opposite directions.

Compared with the existing techniques, the present disclosure has the following advantages.

The present disclosure provides a method and a system for fast high-resolution multi-parametric quantitative magnetic resonance imaging based on fast spin-echo sampling and multiple overlapping-echo technology. The system and the method can achieve multi-parametric quantitative magnetic resonance imaging with the same resolution as fast spin-echo weighted imaging within the same acquisition time and have an ability to resist image distortion caused by inhomogeneous magnetic fields to a certain extent.

DETAILED DESCRIPTION OF THE EMBODIMENTS

The present disclosure is further described below in combination with the accompanying drawings and embodiments.

Figure 1:
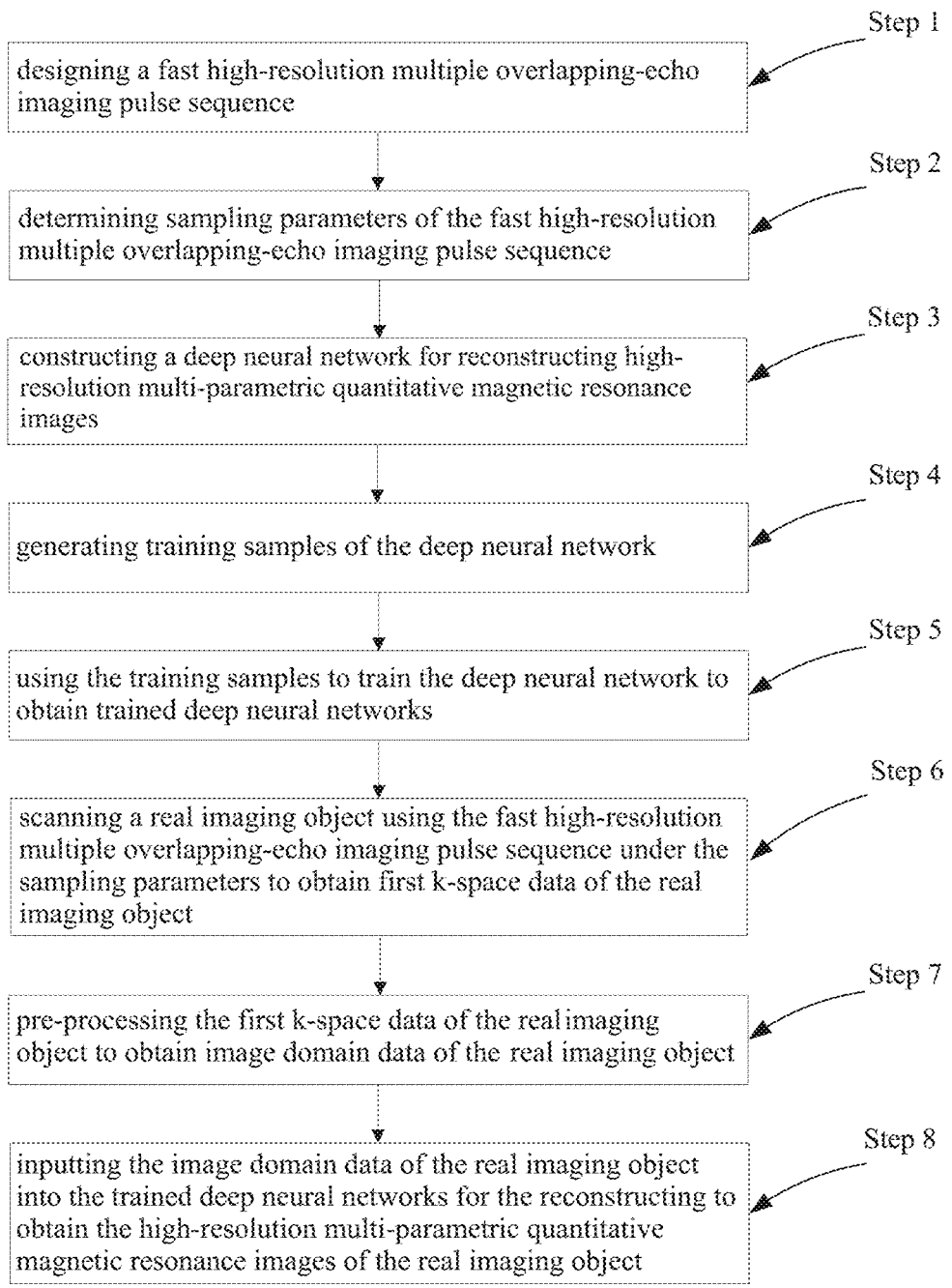
FIG. 1 illustrates a flow diagram of a method of an embodiment of the present disclosure.

Referring to FIG. 1, the present disclosure provides a method for fast high-resolution multi-parametric quantitative magnetic resonance imaging. The method comprises the following steps:

Step 1: designing a fast high-resolution multiple overlapping-echo imaging pulse sequence;

Step 2: determining sampling parameters of the fast high-resolution multiple overlapping-echo imaging pulse sequence;

Step 3: constructing a deep neural network for reconstructing high-resolution multi-parametric quantitative magnetic resonance images;

Step 4: generating training samples of the deep neural network;

Step 5: using the training samples to train the deep neural network to obtain trained deep neural networks;

Step 6: scanning a real imaging object using the fast high-resolution multiple overlapping-echo imaging pulse sequence under the sampling parameters to obtain first k-space data of the real imaging object;

Step 7: pre-processing the first k-space data of the real imaging object to obtain image domain data of the real imaging object;

Step 8: inputting the image domain data of the real imaging object into the trained deep neural networks for the reconstructing to obtain the high-resolution multi-parametric quantitative magnetic resonance images of the real imaging object.

The aforementioned steps will be described in detail.

In the step 1, the designing the fast high-resolution multiple overlapping-echo imaging pulse sequence is designing a fast high-resolution multi-parametric quantitative magnetic resonance imaging pulse sequence.

Figure 2:
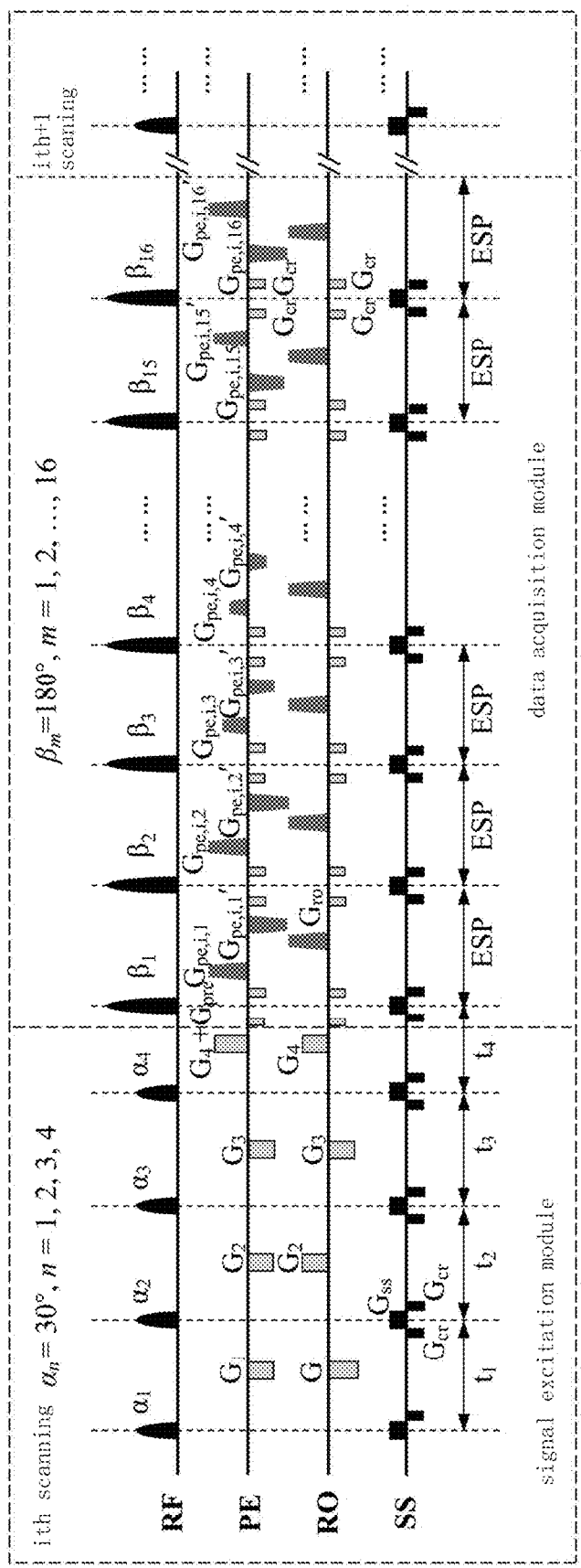
FIG. 2 illustrates a pulse sequence diagram of fast high-resolution multiple overlapping-echo imaging of the embodiment of the present disclosure.

Specifically, referring to FIG. 2, the fast high-resolution multiple overlapping-echo imaging pulse sequence of this embodiment comprises a signal excitation module and a data acquisition module, where RF represents radio frequency pulse, PE represents a phase encoding dimension, RO represents a frequency encoding dimension, and SS represents a slice selection dimension.

The signal excitation module comprises N RF excitation pulses with time intervals $t_n$ and flip angles $\alpha_n$, slice selection gradients $G_{ss}$ corresponding to the N RF excitation pulses, and echo shift gradients $G_n$, wherein n=1, 2, ..., N, and N≥2.

Each of the N RF excitation pulses is combined with a corresponding one of the slice selection gradients $G_{ss}$ in the slice selection dimension for slice selection.

The echo shift gradients $G_n$ are applied after a corresponding RF excitation pulse of the N RF excitation pulses along a frequency encoding dimension and a phase encoding dimension.

The data acquisition module comprises a pre-phase gradient $G_{pre}$, M refocusing pulses with time intervals ESP and flip angles $\beta_m$, crushing gradients $G_{cr}$, phase encoding gradients $G_{pe,i,m}$, frequency encoding gradients $G_{ro}$, and dephase encoding gradients $G_{pe,i,m}'$, wherein i represents an ith scanning, m=1, 2, ..., M, and M≥2.

The pre-phase gradient $G_{pre}$ is applied along the frequency encoding dimension, and a size of the pre-phase gradient $G_{pre}$ is half of a corresponding one of the frequency encoding gradients $G_{ro}$.

The crushing gradients $G_{cr}$ are applied before and after each refocusing pulse of the M refocusing pulses, and sizes and directions of the crushing gradients $G_{cr}$ along the frequency encoding dimension, the phase encoding dimension, and the slice selection dimension are the same.

The phase encoding gradients $G_{pe,i,m}$, the frequency encoding gradients $G_{ro}$, and the dephase encoding gradients $G_{pe,i,m}'$ are applied after each refocusing pulse of the M refocusing pulses. The phase encoding gradient $G_{pe,i,m}$ and the dephase encoding gradient $G_{pe,i,m}'$ have same sizes but opposite directions.

The determining the sampling parameters of the fast high-resolution multiple overlapping-echo imaging pulse sequence in the step 2 comprises the following steps:

Step 21: determining a number N of the N RF excitation pulses and a flip angle $\alpha_n$ of each RF excitation pulse of the N RF excitation pulses.

In this embodiment, the N RF excitation pulses comprises 4 RF excitation pulses, and the flip angle of each RF excitation pulse $\alpha_n$ is 30.

Step 22: determining a composition of echo signals to determine a time interval $t_n$ between two neighboring RF excitation pulses of the 4 RF excitation pulses.

A signal generated by a fourth RF excitation pulse of the 4 RF excitation pulses is collected after a refocusing pulse. In order to eliminate an influence of an inhomogeneous main magnetic field $B_0$ to generate a $T_2$ weighted signal, $t_4$ is set to be 0.5ESP. A signal generated by a second RF excitation pulse of the 4 RF excitation pulses is partially refocused after a third RF excitation pulse. In order to obtain the $T_2$ weighted signal, $t_2$ is set to be equal to $t_3$ to refocus the signal at a time point in which the fourth RF excitation pulse is applied. In order to enable a first RF excitation pulse of the 4 RF excitation pulses to generate a $T_2^*$ weighted signal and to somewhat differ from the signal excited by the third RF excitation pulse with respect to echo time, as well as to avoid a signal attenuation time being too long, $t_1$ should be set within an appropriate range. In this embodiment, $t_1=t_2=t_{3=6}$ ms.

Step 23: determining a position of each of the echo signals in a k-space so as to determine a proportion of the echo shift gradients $G_n$ after each RF excitation pulse.

In this embodiment, the echo shift gradients $G_n$ in the frequency encoding dimension are $G_1=-0.1875\ G_{ro}$, $G_2=0.125\ G_{ro}$, $G_3=-0.1875\ G_{ro}$, and $G_4=0.125\ G_{ro}$, and the echo shift gradients $G_n$ in the phase encoding dimension are $G_1=0.5\ G_{PE}$, $G_2=0.5\ G_{PE}$, $G_3=0.5\ G_{ro}$, and $G_4=-1.5\ G_{PE}$. $G_{ro}$ is the frequency encoding gradient, and $G_{PE}$ is a maximum of the phase encoding gradients $G_{pe,i,m}$.

Step 24: determining a number M of the M refocusing pulses and a flip angle $\beta_m$ of each refocused pulse of the M refocusing pulses.

In this embodiment, the M refocused pulses comprise 16 refocused pulses, and the flip angle $\beta_m$ of each refocused pulse is 180°.

Step 25: determining a phase encoding manner to determine a direction and a proportion of each of the phase encoding gradients and each of the dephase encoding gradients.

In this embodiment, the phase encoding manner adopts interleaved phase encoding.

Step 26: determining a scanning number, an imaging field of view, an imaging matrix, a sampling frequency, a time interval ESP between two neighboring refocusing pulses of the M refocusing pulses, a sampling acceleration factor, and a repetition time TR of the fast high-resolution multiple overlapping-echo imaging pulse sequence so as to determine values of various gradients in the fast high-resolution multiple overlapping-echo imaging pulse sequence.

In the fast high-resolution multiple overlapping-echo imaging pulse sequence of this embodiment, the scanning number is 16, and the imaging field of view is 220 mm×220 mm. The imaging matrix is 256×256, the sampling frequency is 62.464 kHz, the time interval ESP between two neighboring refocusing pulses of the 16 refocusing pulses is 8.84 ms, the sampling acceleration factor is 2, and the repetition time TR is 4000 ms.

The constructing the deep neural network for reconstructing the high-resolution multi-parametric quantitative magnetic resonance images in the step 3 comprises the following steps:

Step 31: constructing a network structure of the deep neural network.

Preferably, in this embodiment, the adopted network structure is a U-net, and the U-net comprises 4 downsampling layers and 4 upsampling layers. Each of the 4 downsampling layers comprises 2 convolutional layers with a kernel size of 3×3, a stride of 1, and a padding of 1, and a pooling layer with a kernel size of 2×2 and a stride of 2. Each of the 2 convolutional layers is activated by a rectified linear unit (ReLU) activation function. Each of the 4 upsampling layers comprises a deconvolutional layer with a kernel size of 3×3 and a stride of 2 and 2 convolutional layers with a kernel size of 3×3, a stride of 1, and a padding of 1. Each of the 2 convolutional layers is activated by the ReLU activation function.

Step 32: determining a number of input channels of the deep neural network and a number of output channels of the deep neural network.

Preferably, in this embodiment, an input of the deep neural network is real parts and imaginary parts of two image domain data, so the number of the input channels is 4. An output of the deep neural network is a proton density image, a $T_2$ quantitative image, a $T_2^*$ quantitative image, or a $dB_0$ image, so the number of the output channels is 1.

Step 33: determining a loss function of the deep neural network.

In this embodiment, the loss function that is used is mean absolute error, that is, a mean of absolute values of differences between outputs of the deep neural network and labels:

$$L = \frac{1}{P}\sum_{j=1}^{P} |f(x_j) - y_j|$$

Wherein L represents a value of the loss function, $\Sigma$ represents a sum, P represents a number of training samples in a training sample set of the deep neural network, $|\cdot|$ represents an operator of taking the absolute value, $f(\ )$ represents a mapping relationship of the deep neural network, $x_j$ represents an input in a jth training sample, and $y_j$ represents a label in the jth training sample.

Figure 3:
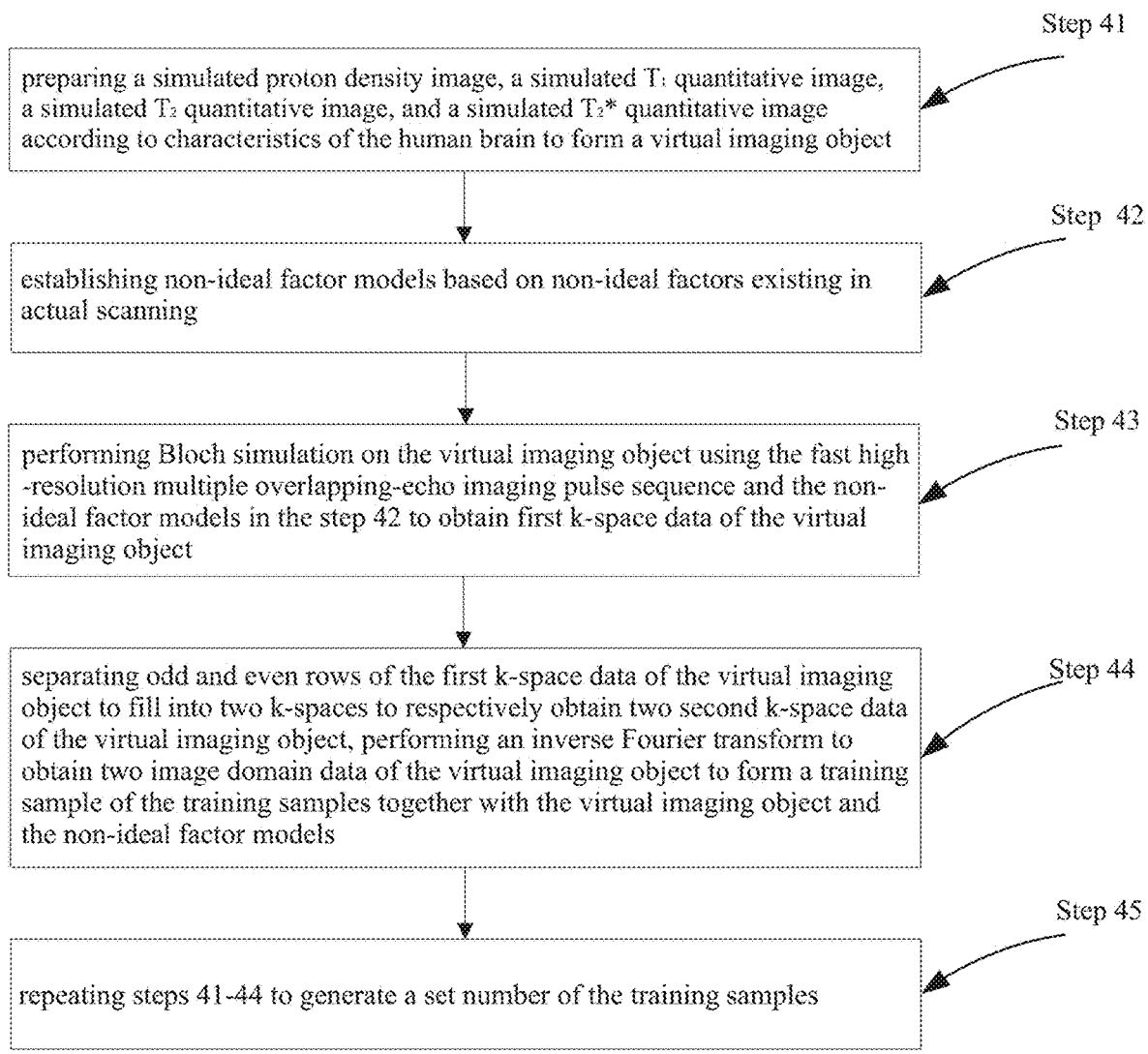
FIG. 3 illustrates a flow diagram for generating training samples of a deep neural network in the embodiment of the present disclosure.

Referring to FIG. 3, the generating training samples of the deep neural network in the step 4 is as follows:

An embodiment using a human brain as a real imaging object is described as follows.

Step 41: preparing a simulated proton density image, a simulated $T_1$ quantitative image, a simulated $T_2$ quantitative image, and a simulated $T_2^*$ quantitative image according to characteristics of the human brain to form a virtual imaging object.

In this embodiment, a magnetic resonance imaging public data set IXI is used to prepare virtual imaging objects. Each object in the magnetic resonance imaging public data set comprises a $T_1$ weighted image, a $T_2$ weighted image, a $T_2^*$ weighted image, and a proton density weighted image. Converting an object in the magnetic resonance imaging public data set into the virtual imaging object comprises the following steps:

Step 411: taking the proton density weighted image as the simulated proton density image of the virtual imaging object;

Step 412: the $T_1$ weighted image is represented as $S_{T1w} \propto PD \times [1-\exp(-TR/T_1)]$, wherein $S_{T1w}$ represents the $T_1$ weighted image, represents proportional to, PD represents a proton density image, and $T_1$ represents the simulated $T_1$ quantitative image. Assuming that TR of the $T_1$ weighted image is $TR_0$, the simulated $T_1$ quantitative image of the virtual imaging object is $T_1 = -TR_0/\ln(1-S_{T1w}/PD)$.

Step 413: the $T_2$ weighted image is represented as $S_{T2*w} = PD \times \exp(-TE/T_2^*)$, wherein $S_{T2w}$ represents the $T_2$ weighted image, TE represents an echo time, and $T_2$ represents the simulated $T_2$ quantitative image. Assuming that TE of the $T_2$ weighted image is $TE_0$, the simulated $T_2$ quantitative image of the virtual imaging object is $T_2 = -TE_0/\ln(S_{T2w}/PD)$.

Step 414: the $T_2^*$ weighted image is represented as $S_{T2*w} = PD \times \exp(-TE/T_2^*)$, wherein $S_{T2*w}$ represents the $T_2^*$ weighted image, and $T_2^*$ represents the simulated $T_2^*$ quantitative image. Assuming that TE of the $T_2^*$ weighted image is $TE_0$, the simulated $T_2^*$ quantitative image of the virtual imaging object is $T_2^* = -TE_0/\ln(S_{T2*w}/PD)$.

The simulated proton density image, the simulated $T_1$ quantitative image, the simulated $T_2$ quantitative image, and the simulated $T_2^*$ quantitative image are packaged to form the virtual imaging object.

Step 42: establishing non-ideal factor models based on non-ideal factors existing in actual scanning is as follows:

In this embodiment, three non-ideal factors, namely non-uniformity of the main magnetic field $B_0$, non-uniformity of an RF field $B_1$, and imperfection of the echo shift gradients $G_n$ are considered.

Step 421: constructing a main magnetic field deviation model $dB_0$ according to non-uniformity of the main magnetic field $B_0$:

$$dB_0 = amp_0 \times \{a_0 X + b_0 Y + c_0 XY + e_0 X^2 + e_0 Y^2 + f_0 XY^2 + g_0 X^2 Y + h_0 \exp[(X-i_0)^2 + (Y-j_0)^2]\}$$

Wherein $amp_0$ controls the non-uniformity of the main magnetic field $B_0$ and follows uniform distribution between [0, 150], $a_0$, $b_0$, $c_0$, $d_0$, $e_0$, $f_0$, $g_0$, $f_0$ follow uniform distribution between [−0.5, 0.5], and $i_0$ and $j_0$ follow uniform distribution between [0.1, 0.9]. X and Y are normalized $dB_0$ coordinate values in a zero-filled model generated according to an image size of the virtual imaging object, and a range of the X and the Y is [−1, 1].

Step 422: constructing an RF field model $B_1$ according to non-uniformity of the RF field $B_1$:

$$B_1 = amp_1 \times \{a_1 X + b_1 Y + c_1 XY + dX^2 + eY^2 + f_1 \exp[(X-i_1)^2 + (Y-j_1)^2]\} + g_1 + 1$$

Wherein $amp_1$ represents non-uniformity of the RF field $B_1$ and follows uniform distribution between [0, 0.6], $a_1$ and $b_1$ follow Gaussian distribution with a mean value of 0 and a variance of 0.5, $c_1$, $d_1$, $e_1$, and $f_1$ follow uniform distribution between [−0.5, 0.5], $g_1$ follows uniform distribution between [−0.05, 0.05], $i_1$ and $j_1$ follow uniform distribution between [0.1, 0.9], X and Y are normalized $B_1$ coordinate values in a zero-filled model generated according to an image size of the virtual imaging object, and a range of the X and the Y is [−1, 1].

Step 423: constructing a model for the echo shift gradients $G_n$ according to imperfection of the echo shift gradients $G_n$:

$$G_n = (1+a_2) G_{n,ideal}$$

Wherein $a_2$ represents a degree of the imperfection of the echo shift gradients $G_n$ and follows uniform distribution between [−0.01, 0.01], $G_n$ represents a size of an nth echo shift gradient of the echo shift gradients $G_n$ actually applied, $G_{n,ideal}$ represents an ideal nth echo shift gradient, and n=1, 2, 3, or 4.

Step 43: performing Bloch simulation on the virtual imaging object using the fast high-resolution multiple overlapping-echo imaging pulse sequence and the non-ideal factor models in the step 42 to obtain first k-space data of the virtual imaging object;

Step 44: separating odd and even rows of the first k-space data of the virtual imaging object to fill into two k-spaces to respectively obtain two second k-space data of the virtual imaging object, performing an inverse Fourier transform to obtain two image domain data of the virtual imaging object to form a training sample of the training samples together with the virtual imaging object and the non-ideal factor models.

Step 45: repeating steps 41-44 to generate a set number of the training samples.

The using the training samples to train the deep neural network to obtain the trained deep neural networks in the step 5 is as follows:

A selected deep neural network is trained by the training samples in batches, and the loss function of the deep neural network is calculated for each of the batches. Parameters of the deep neural network are updated by back-propagation and iteratively updated until the deep neural network converges.

In this embodiment, a number of the training samples of the deep neural network is 2000, wherein 1600 of the training samples are used as a training set of the deep neural network, and 400 of the training samples are used as a test set of the deep neural network. A batch size is 8. The deep neural network converges after 200000 iterations to obtain the trained deep neural networks.

The step 6 is as follows: importing the compiled fast high-resolution multiple overlapping-echo imaging pulse sequence on a magnetic resonance scanner, setting the sampling parameters, and scanning the human brain following standard imaging operation steps to obtain first k-space data of the human brain.

Step 7 is as follows: pre-processing first k-space data of the human brain to obtain image domain data of the human brain comprises the following steps:

Separating collected odd and even rows of the first k-space data of the human brain to respectively fill into two k-spaces according to the phase encoding manner to obtain two second k-space data of the human brain.

Parallel reconstructing the two second k-space data of the human brain.

Performing an inverse Fourier transform for the two second k-space data of the human brain to obtain two image domain data of the human brain.

Figure 4A:
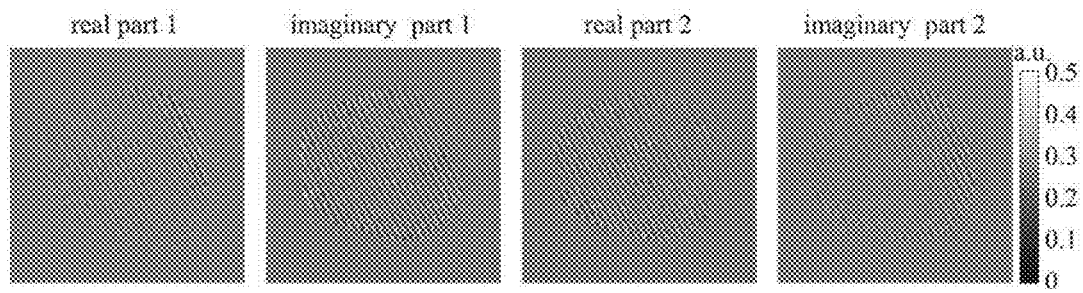
FIGS. 4A, 4B, and 4C illustrate multi-parametric quantitative magnetic resonance images of a human brain obtained in the embodiment of the present disclosure.
Figure 4B:
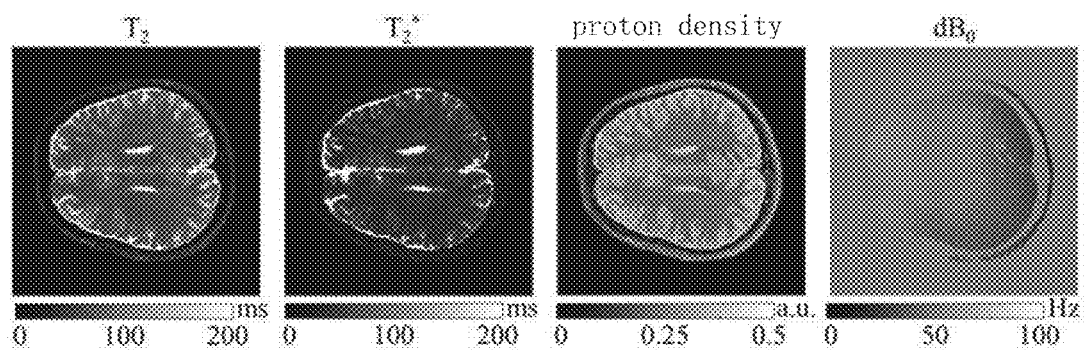
Figure 4C:
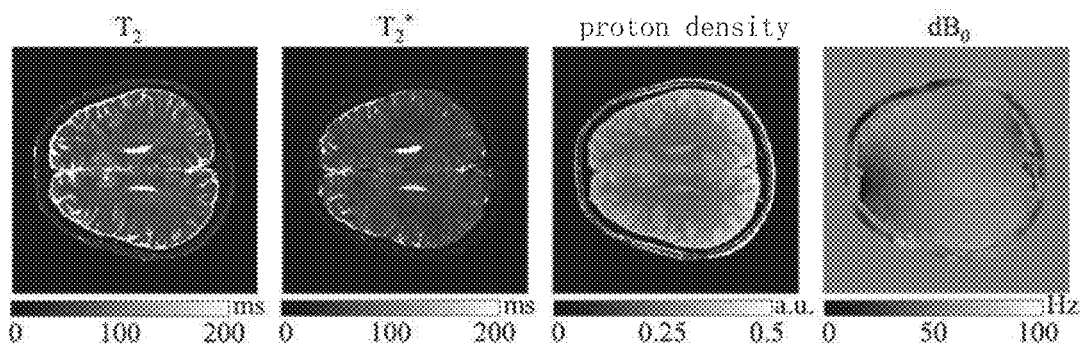

The step 8 comprises the inputting the image domain data of the real imaging object (e.g., the human brain) into the trained deep neural networks for the reconstructing to obtain the high-resolution multi-parametric quantitative magnetic resonance images of the real imaging object (e.g., the human brain). Results of the embodiment are shown in FIGS. 4A, 4B, and 4C. FIG. 4A illustrates real parts and imaginary parts of the two image domain data input into the deep neural network, FIG. 4B illustrates a reconstructed $T_2$ quantitative image, a reconstructed $T_2^*$ quantitative image, a reconstructed proton density image, and a reconstructed $dB_0$ image without visible image distortion, and FIG. 4C illustrates a reference $T_2$ quantitative image, a reference $T_2^*$ quantitative image, a reference proton density image, and a reference $dB_0$ image obtained by fitting multiple weighted images.

Figure 5:
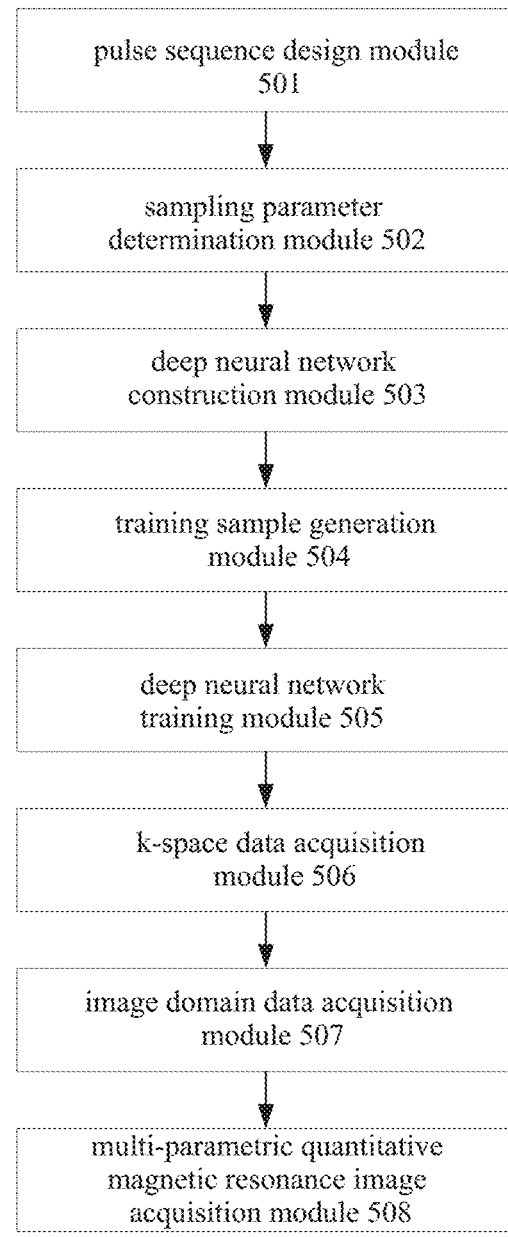
FIG. 5 illustrates a block diagram of a system structure of the embodiment of the present disclosure.

Referring to FIG. 5, as an implementation of the method shown in the aforementioned drawings, this present disclosure provides an embodiment of a system for fast high-resolution multi-parametric quantitative magnetic resonance imaging. The system for the fast high-resolution multi-parametric quantitative magnetic resonance imaging corresponds to the method shown in FIG. 1. The system for the fast high-resolution multi-parametric quantitative magnetic resonance imaging can be specifically applied to various electronic devices.

Specifically, the system for the fast high-resolution multi-parametric quantitative magnetic resonance imaging comprises:

A pulse sequence design module 501 for designing the fast high-resolution multiple overlapping-echo imaging pulse sequence;

A sampling parameter determination module 502 for determining the sampling parameters of the fast high-resolution multiple overlapping-echo imaging pulse sequence;

A deep neural network construction module 503 for constructing the deep neural network for reconstructing the high-resolution multi-parametric quantitative magnetic resonance images;

A training sample generation module 504 for generating the training samples of the deep neural network;

A deep neural network training module 505 for using the training samples to train the deep neural network to obtain the trained deep neural networks;

A k-space data acquisition module 506 for scanning the real imaging object using the fast high-resolution multiple overlapping-echo imaging pulse sequence under the sampling parameters to obtain the first k-space data of the real imaging object;

An image domain data acquisition module 507 for pre-processing the first k-space data of the real imaging object to obtain the image domain data of the real imaging object; and A multi-parametric quantitative magnetic resonance image acquisition module 508 for inputting the image domain data of the real imaging object into the trained deep neural networks for the reconstructing to obtain the high-resolution multi-parametric quantitative magnetic resonance images of the real imaging object.

A specific implementation of the system for the fast high-resolution multi-parametric quantitative magnetic resonance imaging is the same as that of the method for the fast high-resolution multi-parametric quantitative magnetic resonance imaging and will not be repeated in this embodiment.

The aforementioned embodiments are merely to explain the technical concept and the technical features of the present disclosure to enable a person of skill in the art to understand the content of the present disclosure and to implement the present disclosure, and the scope of the disclosure is not limited thereto. Thus, it is intended that the present disclosure cover any modifications and variations provided they are made without departing from the spiritual substance of the present disclosure.

What is claimed is:
1. A method for fast high-resolution multi-parametric quantitative magnetic resonance imaging, comprising:

designing a fast high-resolution multiple overlapping-echo imaging pulse sequence;

determining sampling parameters of the fast high-resolution multiple overlapping-echo imaging pulse sequence;

constructing a deep neural network for reconstructing high-resolution multi-parametric quantitative magnetic resonance images;

generating training samples of the deep neural network;

using the training samples to train the deep neural network to obtain trained deep neural networks;

scanning a real imaging object using the fast high-resolution multiple overlapping-echo imaging pulse sequence under the sampling parameters to obtain first k-space data of the real imaging object;

pre-processing the first k-space data of the real imaging object to obtain image domain data of the real imaging object; and inputting the image domain data of the real imaging object into the trained deep neural networks to obtain high-resolution multi-parametric quantitative magnetic resonance images of the real imaging object, wherein:

the fast high-resolution multiple overlapping-echo imaging pulse sequence comprises a signal excitation module and a data acquisition module, the signal excitation module comprises N radio frequency (RF) excitation pulses with first time intervals ($t_n$) and flip angles ($\alpha_n$), slice selection gradients ($G_{ss}$) corresponding to the N RF excitation pulses, and echo shift gradients ($G_n$), n=1, 2, . . . , N, and N≥2, each of the N RF excitation pulses is combined with a corresponding one of the slice selection gradients ($G_{ss}$) in a slice selection dimension for slice selection, the echo shift gradients ($G_n$) are applied after a corresponding RF excitation pulse of the N RF excitation pulses along a frequency encoding dimension and a phase encoding dimension, the data acquisition module comprises a pre-phase gradient ($G_{pre}$), M refocusing pulses with second time intervals (ESP) and flip angles ($\beta_m$), crushing gradients ($G_{cr}$), phase encoding gradients ($G_{pe,i,m}$), frequency encoding gradients ($G_{ro}$), and dephase encoding gradients ($G_{pe,i,m}'$), i represents an ith scanning, m=1, 2, . . . , M, and M≥2, the pre-phase gradient ($G_{pre}$) is applied along the frequency encoding dimension, and a size of the pre-phase gradient ($G_{pre}$) is half of a corresponding one of the frequency encoding gradients ($G_{ro}$), the crushing gradients ($G_{cr}$) are applied before and after each refocusing pulse of the M refocusing pulses, and sizes and directions of the crushing gradients ($G_{cr}$) along the frequency encoding dimension, the phase encoding dimension, and the slice selection dimension are the same, and the phase encoding gradients ($G_{pe,i,m}$), the frequency encoding gradients ($G_{ro}$), and the dephase encoding gradients ($G_{pe,i,m}'$) are applied after each refocusing pulse of the M refocusing pulses, and the phase encoding gradients ($G_{pe,i,m}$) and the dephase encoding gradients ($G_{pe,i,m}'$) have same sizes but opposite directions.

2. The method according to claim 1, wherein:

the determining sampling parameters of the fast high-resolution multiple overlapping-echo imaging pulse sequence comprises:

determining a number N of the N RF excitation pulses and the flip angle ($\alpha_n$) of each RF excitation pulse of the N RF excitation pulses;

determining a composition of echo signals to determine the first time interval ($t_n$) between two neighboring RF excitation pulses of the N RF excitation pulses;

determining a position of each of the echo signals in a k-space so as to determine a proportion of the echo shift gradients ($G_n$) after each RF excitation pulse of the N RF excitation pulses;

determining a number M of the M refocusing pulses and the flip angle ($\beta_m$) of each refocused pulse of the M refocusing pulses;

determining a phase encoding manner to determine a direction and a proportion of each of the phase encoding gradients ($G_{pe,i,m}$) and each of the dephase encoding gradients ($G_{pe,i,m}'$); and determining a scanning number, an imaging field of view, an imaging matrix, a sampling frequency, the second time interval (ESP) between two neighboring refocusing pulses of the M refocusing pulses, a sampling acceleration factor, and a repetition time (TR) of the fast high-resolution multiple overlapping-echo imaging pulse sequence so as to determine values of various gradients in the fast high-resolution multiple overlapping-echo imaging pulse sequence.

3. The method according to claim 1, wherein:

the constructing a deep neural network for reconstructing high-resolution multi-parametric quantitative magnetic resonance images comprises:

constructing a network structure of the deep neural network;

constructing a number of input channels of the deep neural network and a number of output channels of the deep neural network; and constructing a loss function of the deep neural network.

4. The method according to claim 1, wherein:

the generating training samples of the deep neural network comprises:

preparing a simulated proton density image, a first simulated quantitative image ($T_1$), a second simulated quantitative image ($T_2$), and a third simulated quantitative image ($T_2^*$) according to characteristics of the real imaging object to form a virtual imaging object;

establishing non-ideal factor models based on non-ideal factors existing in actual scanning;

performing Bloch simulation on the virtual imaging object using the fast high-resolution multiple overlapping-echo imaging pulse sequence and the non-ideal factor models to obtain first k-space data of the virtual imaging object;

separating odd and even rows of the first k-space data of the virtual imaging object to fill into two k-spaces to respectively obtain two second k-space data of the virtual imaging object, performing an inverse Fourier transform to obtain image domain data of the virtual imaging object to form a training sample of the training samples together with the virtual imaging object and the non-ideal factor models; and repeating the aforementioned steps to generate a set number of the training samples.

5. The method according to claim 1, wherein:

the pre-processing the first k-space data of the real imaging object to obtain the image domain data of the real imaging object comprises:

separating collected odd and even rows of the first k-space data of the real imaging object to respectively fill into two k-spaces according to the phase encoding manner to obtain two second k-space data of the real imaging object;

parallel reconstructing the two second k-space data of the real imaging object provided that a sampling acceleration factor is more than 1; and performing an inverse Fourier transform for the two second k-space data to obtain the image domain data of the real imaging object.

6. A system for fast high-resolution multi-parametric quantitative magnetic resonance imaging, comprising:

a pulse sequence design module for designing a fast high-resolution multiple overlapping-echo imaging pulse sequence;

a sampling parameter determination module for determining sampling parameters of the fast high-resolution multiple overlapping-echo imaging pulse sequence;

a deep neural network construction module for constructing a deep neural network for reconstructing high-resolution multi-parametric quantitative magnetic resonance images;

a training sample generation module for generating training samples of the deep neural network;

a deep neural network training module for using the training samples to train the deep neural network to obtain trained deep neural networks;

a k-space data acquisition module for scanning a real imaging object using the fast high-resolution multiple overlapping-echo imaging pulse sequence under the sampling parameters to obtain k-space data of the real imaging object;

an image domain data acquisition module for pre-processing the k-space data of the real imaging object to obtain image domain data of the real imaging object; and a multi-parametric quantitative magnetic resonance image acquisition module for inputting the image domain data of the real imaging object into the trained deep neural networks to obtain high-resolution multi-parametric quantitative magnetic resonance images of the real imaging object, wherein:

the fast high-resolution multiple overlapping-echo imaging pulse sequence comprises a signal excitation module and a data acquisition module, the signal excitation module comprises N radio frequency (RF) excitation pulses with first time intervals ($t_n$) and flip angles ($\alpha_n$), slice selection gradients ($G_{ss}$) corresponding to the N RF excitation pulses, and echo shift gradients ($G_n$), n=1, 2, ..., N, and N≥2, each of the N RF excitation pulses is combined with a corresponding one of the slice selection gradients ($G_{ss}$) in a slice selection dimension for slice selection, the echo shift gradients ($G_n$) are applied after a corresponding RF excitation pulse of the N RF excitation pulses along a frequency encoding dimension and a phase encoding dimension, the data acquisition module comprises a pre-phase gradient ($G_{pre}$), M refocusing pulses with second time intervals (ESP) and flip angles ($\beta_m$), crushing gradients ($G_{cr}$), phase encoding gradients ($G_{pe,i,m}$), frequency encoding gradients ($G_{ro}$), and dephase encoding gradients ($G_{pe,i,m}'$), i represents an ith scanning, m=1, 2, ..., M, and M≥2, the pre-phase gradient ($G_{pre}$) is applied along the frequency encoding dimension, and a size of the pre-phase gradient ($G_{pre}$) is half of a corresponding one of the frequency encoding gradients ($G_{ro}$), the crushing gradients ($G_{cr}$) are applied before and after each refocusing pulse of the M refocusing pulses, and sizes and directions of the crushing gradients ($G_{cr}$) along the frequency encoding dimension, the phase encoding dimension, and the slice selection dimension are the same, and the phase encoding gradients ($G_{pe,i,m}$), the frequency encoding gradients ($G_{ro}$), and the dephase encoding gradients ($G_{pe,i,m}'$) are applied after each refocusing pulse of the M refocusing pulses, and the phase encoding gradients ($G_{pe,i,m}$) and the dephase encoding gradients ($G_{pe,i,m}'$) have same sizes but opposite directions.

* * * * *